(12) United States Patent
Walter

(10) Patent No.: US 8,056,456 B2
(45) Date of Patent: Nov. 15, 2011

(54) APPARATUS FOR PRODUCING THIN SECTIONS

(75) Inventor: Roland Walter, Reilingen (DE)

(73) Assignee: Leica Biosystems Nussloch GmbH, Nussloch (DE)

( * ) Notice: Subject to any disclaimer, the term of this patent is extended or adjusted under 35 U.S.C. 154(b) by 399 days.

(21) Appl. No.: 12/120,777

(22) Filed: May 15, 2008

(65) Prior Publication Data

US 2008/0286859 A1  Nov. 20, 2008

(30) Foreign Application Priority Data

May 19, 2007 (DE) .................... 20 2007 007 160 U

(51) Int. Cl.
*B26D 5/28* (2006.01)

(52) U.S. Cl. .......................... 83/76.8; 83/365; 83/915.5

(58) Field of Classification Search .................. 83/365, 83/915.5, 935, 76.6–76.9; 356/614, 625, 356/630, 634, 635; 250/559.19, 559.28, 250/559.29
See application file for complete search history.

(56) References Cited

U.S. PATENT DOCUMENTS

| | | | | | |
|---|---|---|---|---|---|
| 3,845,659 | A | * | 11/1974 | Wikefeldt et al. | 73/862.06 |
| 4,511,224 | A | * | 4/1985 | Sitte et al. | 83/167 |
| 4,532,838 | A | * | 8/1985 | Soderkvist | 83/13 |
| 5,141,871 | A | * | 8/1992 | Kureshy et al. | 436/47 |
| 5,181,443 | A | * | 1/1993 | Sitte et al. | 83/72 |
| 5,226,335 | A | * | 7/1993 | Sitte et al. | 83/74 |
| 5,282,404 | A | * | 2/1994 | Leighton et al. | 83/13 |
| 5,287,759 | A | * | 2/1994 | Kaneda | 73/865.8 |
| 5,309,223 | A | * | 5/1994 | Konicek et al. | 356/621 |
| 5,535,654 | A | * | 7/1996 | Niesporek et al. | 83/364 |
| 5,559,727 | A | * | 9/1996 | Deley et al. | 700/279 |
| 5,761,977 | A | * | 6/1998 | Jakobi et al. | 83/13 |
| 6,253,653 | B1 | * | 7/2001 | Walter et al. | 83/703 |
| 6,330,348 | B1 | * | 12/2001 | Kerschmann et al. | 382/128 |
| 6,568,307 | B1 | * | 5/2003 | Gunther et al. | 83/367 |
| 6,634,268 | B1 | * | 10/2003 | Guenther et al. | 83/13 |
| 6,635,894 | B1 | * | 10/2003 | Stimpson et al. | 250/559.12 |
| 6,734,981 | B1 | * | 5/2004 | Tatum et al. | 356/621 |
| 6,744,572 | B1 | * | 6/2004 | McCormick | 359/799 |
| 6,753,519 | B2 | * | 6/2004 | Gombert | 250/221 |
| 7,027,166 | B2 | * | 4/2006 | Luetche et al. | 356/615 |
| 7,084,989 | B2 | * | 8/2006 | Johannesson et al. | 356/601 |
| 7,217,071 | B2 | * | 5/2007 | Bayha et al. | 409/131 |
| 2004/0124378 | A1 | * | 7/2004 | Lihl et al. | 250/559.12 |
| 2005/0072285 | A1 | * | 4/2005 | Lang et al. | 83/520 |
| 2006/0145101 | A1 | * | 7/2006 | De Coi | 250/559.12 |
| 2006/0156878 | A1 | * | 7/2006 | Faires et al. | 83/13 |
| 2007/0291283 | A1 | * | 12/2007 | Sakai | 356/630 |
| 2009/0199716 | A1 | * | 8/2009 | Schmitt et al. | 95/278 |
| 2009/0244537 | A1 | * | 10/2009 | Murooka et al. | 356/364 |
| 2009/0244551 | A1 | * | 10/2009 | Lutz | 356/630 |
| 2010/0147120 | A1 | * | 6/2010 | Walter | 83/13 |

OTHER PUBLICATIONS

Freedom Technologies- Maclab Series. Published online and dated Aug. 28, 2001. http://www.laser-view.com/Meclab%20Bench%20Gauges.*

* cited by examiner

*Primary Examiner* — Sean Michalski
(74) *Attorney, Agent, or Firm* — Hodgson Russ LLP

(57) ABSTRACT

An apparatus for producing flat thin sections of a specimen (3) comprises a blade edge (7), a specimen carrier (4), a drive device (14) for producing a relative motion between the blade edge (7) and the specimen carrier (4) in a sectioning plane (5), and a light light-ribbon micrometer (8) arranged between the blade edge (7) and the specimen (3), wherein the light-ribbon micrometer (8) is arranged at a fixed distance (d) relative to the blade edge (7) and generates a light-ribbon in a plane perpendicular to the sectioning plane. A coding device (13) may be associated with the drive device (14) for controlling an alternating drive as a function of the distance (d) and of signals generated by the light-ribbon micrometer (8).

6 Claims, 2 Drawing Sheets

APPARATUS FOR PRODUCING THIN SECTIONS

CROSS REFERENCE TO RELATED APPLICATIONS

This application claims priority of German patent application 20 2007 007 160.4 filed May 19, 2007, which is incorporated by reference herein.

FIELD OF THE INVENTION

The invention relates to an apparatus for producing flat thin sections of a specimen, having a blade edge, a specimen held on a specimen carrier, a drive device for producing a relative motion between the blade edge and specimen carrier in a sectioning plane, and a light barrier arranged between the blade edge and specimen.

BACKGROUND OF THE INVENTION

Apparatuses of this kind are known, in particular, as sliding, rotary, or rotating disc microtomes depending on the direction of the relative motion, or as ultramicrotomes depending on the cut thickness. To produce the section, either the specimen is measurably shifted with respect to the stationary blade edge, or the blade edge is measurably shifted with respect to the stationary specimen. The thickness of the section is adjusted by measurably stepwise displacement of the blade edge or of the specimen holder perpendicularly to the current sectioning plane.

The approaching motion between the blade edge and specimen is referred to as an "advance." The portion of the sectioning stroke during which the specimen is located in the engagement region of the blade edge is referred to as a "sectioning window." To ensure good sectioning quality, the sectioning speed in the region of the sectioning window must not be too high. In the advance region, on the other hand, the positioning speeds can be as high as possible so as to minimize the total processing time.

Known apparatuses are therefore usually equipped with programmable alternating drives that permit the setting of different advance speeds and sectioning speeds. Once a blade edge and a specimen to be processed have been placed into the apparatus, the travel lengths for advancing and for sectioning the specimen should be capable of being detected and set by said apparatus in as automatic a fashion as possible.

It is known from DE 102 58 553 B4 (corresponding to US 2004/0124378) to arrange for this purpose, between the blade edge and specimen holder, a light barrier that contains a transmitter for producing a thin light beam bundle and a detector for receiving the light beam bundle. The light beam bundle is arranged parallel to the blade edge and spaced away therefrom at the same height. As long as the relative position between the specimen and blade edge is not known, a relative motion between the specimen and blade edge in a plane parallel to the sectioning plane must also be performed during advance, in order to ensure that specimens of different sizes arrive in the region of the light barrier.

A coding unit associated with the alternating drive ascertains, from the known distance between the light barrier and blade edge, the advance motion that is still possible, and switches over to the sectioning speed. The duration of the interruption of the light barrier during sectioning is proportional to the size of the sectioning window, and can likewise be ascertained by the coding unit and used for the next sectioning operation.

The disadvantage of the known apparatus is that a plurality of stepwise advances, combined in each case with a sectioning stroke, must be carried out in order to detect the light barrier. This requires a relatively large expenditure of time.

SUMMARY OF THE INVENTION

The underlying object of the invention was therefore to accelerate the operation of automatically recognizing the light barrier, and thereby further to shorten the processing time.

This object is achieved according to the invention, in an apparatus of the kind cited initially, in that a light-ribbon micrometer, which is arranged at a fixed distance relative to the blade edge and perpendicular to the sectioning plane, is provided as a light barrier.

A light-ribbon micrometer produces a flat ribbon of light on the transmitter side, and contains on the detector side a plurality of discrete detector elements that enable a measurable determination of the portion of the light ribbon interrupted by a specimen. The width of the light ribbon extends away from the blade edge toward the specimen. Depending on the width of the light ribbon, the specimen therefore enters the light ribbon after only a few advance and/or sectioning strokes, and interrupts a portion of the light ribbon. From the known distance between the light-ribbon micrometer and the blade edge, and from the unoccluded region of the light ribbon toward the blade edge, the absolute distance between the specimen and the blade edge can be determined and the further advance region can be ascertained. Once the specimen has passed completely through the light ribbon, occlusion of the detector region is terminated. The specimen's travel length in the sectioning plane, corresponding to the time during which the light ribbon is occluded, can be ascertained by suitable coding means on the drive device, so that taking into account the distance to the blade edge, the size of the cutting window is therefore also immediately known. The remainder of the advance and sectioning procedure can be controlled automatically. It is advantageous for this purpose if the drive device has associated with it a coding device for controlling an alternating drive as a function of the distance to the blade edge, and of the signals of the light-ribbon micrometer.

BRIEF DESCRIPTION OF THE DRAWING VIEWS

The invention is described below with reference to schematically depicted exemplifying embodiments. In the Figures.

DETAILED DESCRIPTION OF THE INVENTION

Figure 1:
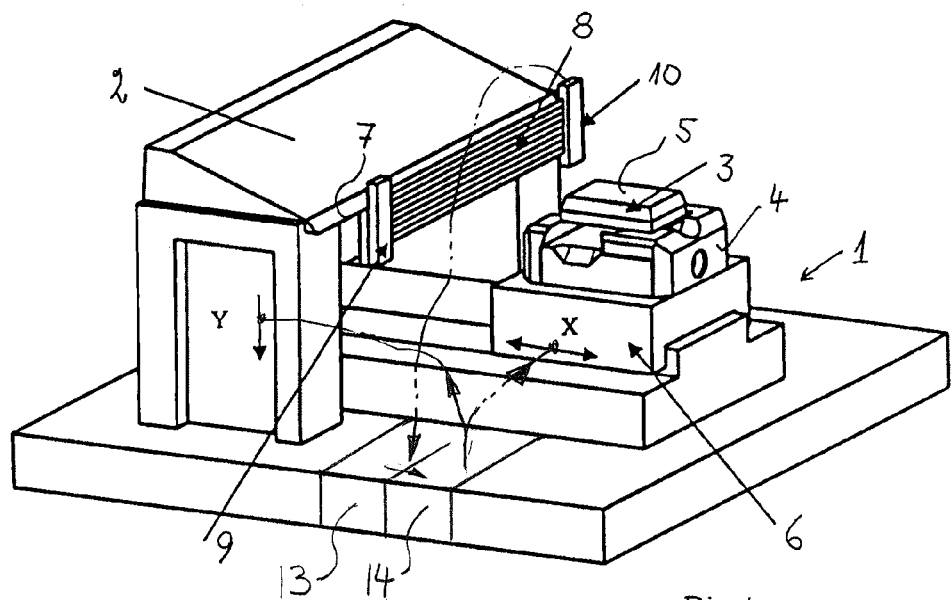
FIG. 1 shows a sliding microtome having a light-ribbon micrometer.

FIG. 1 shows a sliding microtome 1 having a blade carrier 2. A specimen 3 is mounted on a specimen carrier 4 that can be moved in the X direction in oscillating fashion in sectioning plane 5, using a slide 6, past a blade edge 7. The advancing motion between specimen 3 and blade edge 7 can be accomplished, in principle, by lowering blade carrier 2 in the Y direction or by raising specimen carrier 4 in the Y direction. Advance occurs in steps, after each sectioning stroke in the X direction.

A light-ribbon micrometer 8 is arranged perpendicular to sectioning plane 5 at a defined distance d (not further depicted here) from blade edge 7. Light-ribbon micrometer 8 comprises a light-ribbon transmitter 9 and a precise spatially resolving receiver unit 10.

Figure 2:
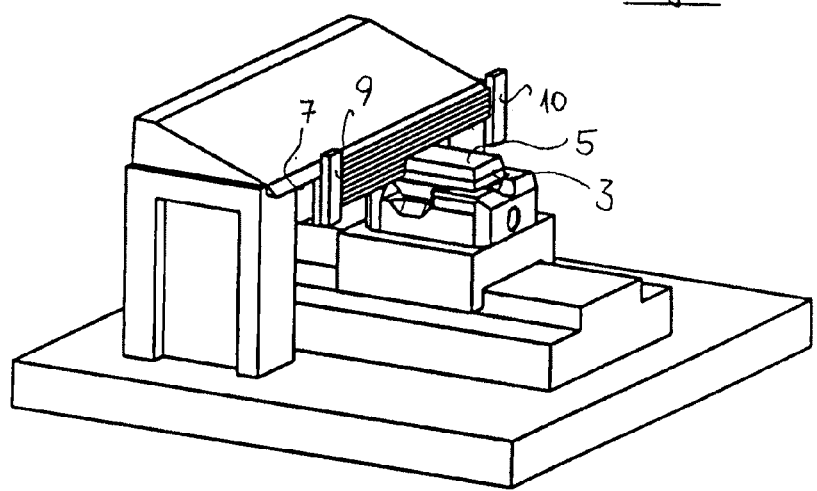
FIG. 2 shows the same arrangement with a large-area specimen in the light ribbon.

FIG. 2 shows the entry of specimen 3 into the light ribbon generated by light-ribbon transmitter 9, and the resulting occlusion of a region on receiver unit 10. Only the portion located in the region of sectioning plane 5, i.e. the highest point on specimen 3, is taken into account. At the point in time when specimen 3 enters the light ribbon, the front edge of specimen 3 is still a distance d away from the vertical projection of blade edge 7. The sectioning stroke can first be stopped. If the vertical location of blade edge 7 relative to an element of receiver unit 10 is known as a device constant, it is now possible, for example, to advance blade edge 7 in the Y direction into sectioning plane 5 in consideration of the desired section thickness. The sectioning operation can then be continued at an adapted sectioning speed.

Like the entry of specimen 3 into the light ribbon, the exit of the rear edge of specimen 3 out of the light ribbon, and subsequently out of the blade region, at the end of the sectioning stroke is recorded, and acceleration of the linear stroke motion is correspondingly initiated. The sectioning window is thereby automatically set at the first sectioning stroke, and is retained for the subsequent sectioning actions.

Figure 3:
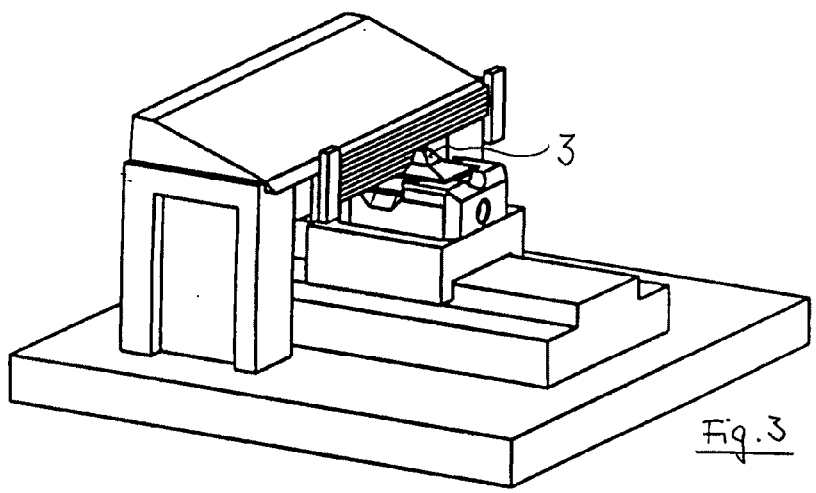
FIG. 3 shows the same arrangement with a small-area specimen in the light ribbon.

FIG. 3 shows a pyramidal specimen 3. With such specimens, it is evident that the size of the sectioning window changes as the sectioning depth increases. For this purpose, a measurement can be accomplished at each sectioning stroke so that the sectioning window is automatically adapted. Time-consuming individual adaptation of the sectioning window can thereby be omitted.

Figure 4:
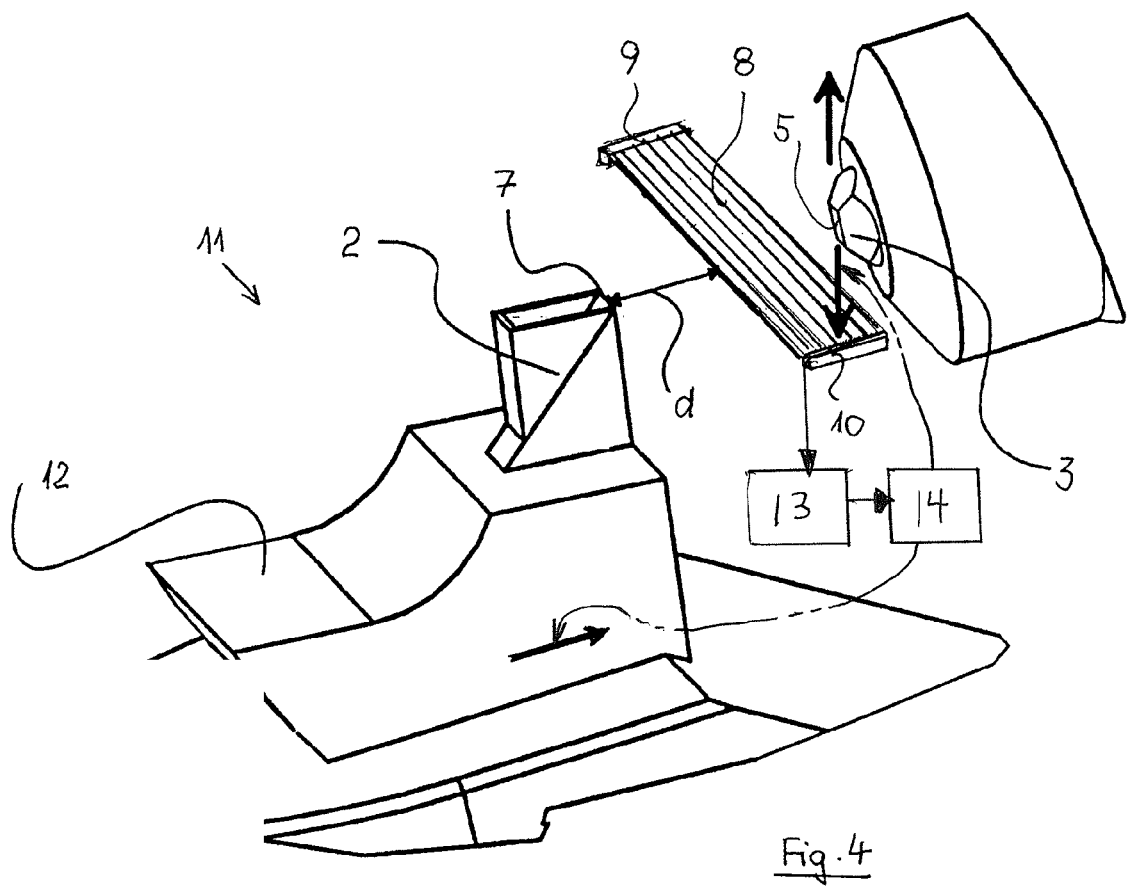
FIG. 4 shows a rotary microtome having a light-ribbon micrometer.

FIG. 4 shows a rotary microtome 11 in which specimen 3 is moved oscillatingly up and down in the arrow directions. Blade carrier 2 is advanced onto specimen 3 using a blade slide 12. Arranged at a fixed distance d in front of blade edge 7 is light-ribbon micrometer 8, which is therefore also shifted forward upon the advance of blade edge 7. If the light ribbon is sufficiently wide, blade edge 7 can be coarsely advanced in manual fashion, after the mounting of specimen 3, until the highest point on specimen 3 enters the light ribbon. With a single sectioning stroke it is thus possible both to ascertain the distance of blade edge 7 from sectioning plane 5, and to determine the size of the sectioning window. The further adjustments can be performed automatically.

As represented schematically in FIGS. 1 and 4, a drive device 14 for producing a relative motion between blade edge 7 and specimen carrier 4 in sectioning plane 5 has associated with it a coding device 13 for controlling an alternating drive as a function of the distance to the blade edge, and of signals generated by light-ribbon micrometer 8, wherein the alternating drive provides different advance and sectioning speeds.

What is claimed is:

1. A microtome for producing flat thin sections of a specimen, the microtome comprising:
   a blade edge;
   a specimen carrier for holding the specimen;
   a drive device for producing a relative motion between the blade edge and the specimen carrier in a horizontal sectioning plane;
   a light-ribbon micrometer arranged between the blade edge and the specimen, wherein the light-ribbon micrometer generates a light-ribbon in a plane perpendicular to the sectioning plane, wherein the plane of the light ribbon is located at a fixed horizontal distance relative to the blade edge, the light-ribbon micrometer including a receiver unit having a plurality of discrete detector elements arranged in the plane of the light ribbon, wherein a known vertical location of the blade edge relative one of the plurality of detector elements defines a device constant; and
   a coding device that measures a horizontal length of the specimen in the sectioning plane based on signals generated by the light-ribbon micrometer from movement of the specimen completely through the light ribbon micrometer by the drive device and the specimen carrier;
   wherein said coding device is associated with the drive device for controlling an alternating drive as a function of the fixed horizontal distance, of the device constant, of the measured horizontal length of the specimen and of specimen position signals generated by the light-ribbon micrometer.

2. The microtome of claim 1, wherein the horizontal length is determined by ascertaining a time at least one of the detector elements is occluded while the specimen is moved through the light-ribbon micrometer.

3. The microtome of claim 1, wherein the coding device is further adapted to determine a cutting stroke length for the drive device based upon the horizontal length and the fixed horizontal distance.

4. The microtome of claim 1, wherein the coding device is further adapted to determine a highest point of the specimen based on signals generated by the light-ribbon micrometer corresponding to movement of the specimen completely through the light-ribbon micrometer by the drive device and the specimen carrier.

5. The microtome of claim 4, wherein the apparatus is operable to adjust the vertical distance between the blade edge and the specimen carrier to set a desired section thickness based on the determined highest point of the specimen and the device constant.

6. The microtome of claim 5, wherein for a specimen having a pyramidal shape the coding device is further adapted to adjust the cutting stroke length for the drive device for each successive sectioning cut.

* * * * *